(12) United States Patent
Brauers et al.

(10) Patent No.: US 8,123,685 B2
(45) Date of Patent: Feb. 28, 2012

(54) SYSTEM FOR MONITORING A NUMBER OF DIFFERENT PARAMETERS OF A PATIENT IN A BED

(75) Inventors: Andreas Brauers, Aachen (DE); Ralf Dorscheid, Kerkrade (NL); Frank Johnen, Juelich-Koslar (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 487 days.

(21) Appl. No.: 12/089,918

(22) PCT Filed: Sep. 29, 2006

(86) PCT No.: PCT/IB2006/053562
§ 371 (c)(1),
(2), (4) Date: Apr. 11, 2008

(87) PCT Pub. No.: WO2007/042960
PCT Pub. Date: Apr. 19, 2007

(65) Prior Publication Data
US 2008/0249378 A1 Oct. 9, 2008

(30) Foreign Application Priority Data
Oct. 11, 2005 (EP) .................................. 05109419

(51) Int. Cl.
*A61B 5/00* (2006.01)
*A61B 5/02* (2006.01)
*A61B 5/08* (2006.01)
*A61B 5/103* (2006.01)
*A61B 5/117* (2006.01)
*A47C 31/00* (2006.01)
*A47B 71/00* (2006.01)

(52) U.S. Cl. ........ 600/301; 600/481; 600/534; 600/587; 600/595; 5/11; 5/600

(58) Field of Classification Search ......... 5/11, 600–651
See application file for complete search history.

(56) References Cited

U.S. PATENT DOCUMENTS
5,859,390 A   1/1999   Stafford et al.
(Continued)

FOREIGN PATENT DOCUMENTS
| EP | 0838659 A2 | 4/1998 |
| JP | 10014889 A | 1/1998 |
| WO | WO2004018986 A1 | 3/2004 |
| WO | WO2006111889 A1 | 10/2006 |

OTHER PUBLICATIONS

Van Der Loos et al: "Development of Sensate and Robotic Bed Technologies for Vital Signs Monitoring and Sleep Quality Improvement"; Autonomous Robots 15, 2003, pp. 67-79, Kluwer Academic Publishers, The Netherlands. Spillman et al: "A 'Smart' Bed for Non-Intrusive Monitoring of Patient Physiological Factors": Meas. Sci. Technol. 15, pp. 1614-1620, Aug. 2004.

*Primary Examiner* — Sam Yao
*Assistant Examiner* — Shirley Jian

(57) ABSTRACT

In order to provide a simple and reliable monitoring technique for a number of different parameters of a patient in a bed (2), a system (1) is provided, said system (1) comprising: at least one first sensor device (25) adapted to measure a first force component acting in a first direction (12), said first force component corresponding to a first parameter of the patient, at least one second sensor device (36) adapted to measure a second force component acting in a second direction (13, 14), said second force component corresponding to a second parameter of the patient, and a data device (16) adapted to acquire the measured data from the at least one first sensor device (25) and the at least one second sensor device (36) and to process those data in order to provide information about the number of parameters of the patient.

17 Claims, 4 Drawing Sheets

U.S. PATENT DOCUMENTS

| | | | |
|---|---|---|---|
| 6,320,510 B2 * | 11/2001 | Menkedick et al. | 340/573.1 |
| 6,362,439 B1 | 3/2002 | Reichow | |
| 6,832,987 B2 * | 12/2004 | David et al. | 600/300 |
| 2003/0114736 A1 * | 6/2003 | Reed et al. | 600/300 |
| 2004/0111045 A1 | 6/2004 | Sullivan et al. | |
| 2005/0113721 A1 | 5/2005 | Reed et al. | |
| 2005/0124864 A1 * | 6/2005 | Mack et al. | 600/300 |

\* cited by examiner

SYSTEM FOR MONITORING A NUMBER OF DIFFERENT PARAMETERS OF A PATIENT IN A BED

The present invention relates to a system for monitoring a number of parameters of a patient in a bed. Furthermore the present invention relates to a method for operating such a system and to a computer program to be executed in a computer.

Monitoring of patients during their sleep is a standard activity in different situations, mostly applied in hospital settings. Depending on the diagnosis, different parameters are monitored. Parameters that often need monitoring are weight, heart rate, breathing rate and breathing abnormalities, as well as special movement patterns during the sleep. It requires significant technical effort and different techniques to measure these quantities.

From the prior art different techniques are known to acquire information on cardio pulmonary performance, e.g. using pressure sensitive sheets in a bed. Other techniques provide solutions for measuring a patient's weight by introducing scales under or in the bedposts. Such a solution is described for example in the U.S. Pat. No. 5,859,390. However, a simple and reliable approach for a combined measuring of weight and other parameters of the patient is not known.

In hospital settings additional requirements must be met. A typical hospital bed does not provide a static bedpost but is equipped with a hydraulic system for manipulating the position of the patient, the bedstead usually is used for attaching devices to it (e.g. monitoring devices, urinal). Furthermore hospital beds have to be mobile and changing mattresses should not involve any hassle with monitoring equipment.

It is an object of the present invention to provide a simple and reliable monitoring technique for a number of different parameters of a patient in a bed.

This object is achieved according to the invention by a system for monitoring a number of different parameters of a patient in a bed, the system comprising at least one first sensor device adapted to measure a first force component acting in a first direction, said first force component corresponding to a first parameter of the patient, at least one second sensor device adapted to measure a second force component acting in a second direction, said second force component corresponding to a second parameter of the patient, and a data device adapted to acquire the measured data from the at least one first sensor device and the at least one second sensor device and to process those data in order to provide information about the number of parameters of the patient.

The object of the present invention is also achieved by a method of monitoring a number of different parameters of a patient in a bed, the method comprising the steps of measuring at least one first force component acting in a first direction, said first force component corresponding to a first parameter of the patient, measuring at least one second force component acting in a second direction, said second force component corresponding to a second parameter of the patient, and acquiring the measured data and processing those data in order to provide information about the number of parameters of the patient.

The object of the present invention is also achieved by a computer program for monitoring a number of different parameters of a patient in a bed, the computer program comprising computer instructions to acquire measured data from at least one first sensor device adapted to measure a first force component acting in a first direction, said first force component corresponding to a first parameter of the patient, and from at least one second sensor device adapted to measure a second force component acting in a second direction, said second force component corresponding to a second parameter of the patient, and computer instructions to process those data in order to provide information about the number of parameters of the patient, when the computer program is executed in the computer. The technical effects necessary according to the invention can thus be realized on the basis of the instructions of the computer program in accordance with the invention. Such a computer program can be stored on a carrier such as a CD-ROM or it can be available over the internet or another computer network. Prior to executing, the computer program is loaded into the computer by reading the computer program from the carrier, for example by means of a CD-ROM player, or from the internet, and storing it in the memory of the computer. The computer includes inter alia a central processor unit (CPU), a bus system, memory means, e.g. RAM or ROM etc., storage means, e.g. floppy disk or hard disk units etc. and input/output units. Alternatively, the inventive method could be implemented in hardware, e.g. using one or more integrated circuits.

A core idea of the invention is to provide a technique for a combined measurement of different patient related parameters using exclusively force sensor devices. Mechanical force sensors are simple and robust low cost devices. An idea of the present invention is to utilize said force sensor devices to obtain information about patient parameters which, in prior art solutions, are obtained using other types of sensors, e.g. ECG electrodes or the like. In particular with the present invention it is possible to obtain not only information about the patient's weight, but also information about the patient's respiration and heart rate. By utilizing different force sensors for determining different parameters, highly accurate and reliable measurements can be carried out without interferences. The invention can also be used for monitoring the sleep quality of a healthy person.

A bed according to the present invention is defined as a surface or any other device to rest on or to sit on etc., e.g. a conventional bed, a hospital bed, a couch, a conventional chair, a dentist's chair, a wheelchair, an (operating) table, etc. However, the present invention is preferably applicable in hospital settings. Accordingly the bed is preferably a hospital bed.

These and other aspects of the invention will be further elaborated on the basis of the following embodiments which are defined in the dependent claims.

According to a preferred embodiment of the invention for the bed at least one joint sensor unit is provided, said sensor unit comprising a first sensor device and a second sensor device. Such a compact sensor unit can be installed in a very easy way and therefore reduces the installation costs. Preferably, the bed comprises a base frame and a patient support, the patient support being connected to the base frame. For the patient support any kind of surface may be used. In this case, the sensor unit is preferably adapted to be an inherent part of the base frame. By this means, the monitoring system is completely unobtrusive to the patient and to caregivers. Furthermore the presence of the sensor unit itself and the measuring process do not affect clinical routines like manipulations to the bed (e.g. a height adjustment of the patient support).

In an alternative embodiment the sensor unit is adapted to be an inherent part of the patient support. However, since the patient support in a hospital bed is usually connected to the base frame in an adjustable way (e.g. for providing a height adjustment), an integration of the sensor unit into the patient support requires a greater effort for measuring and/or data processing, because the directions of the force components may vary depending on the variable position of the patient support. Thus, for an unobtrusive monitoring of said parameters, the integration into the base frame is preferred.

According to another preferred embodiment of the invention the sensor devices are provided in a specific arrangement. There are four different arrangements: In a first arrangement the first sensor device is (rigidly) attached to the patient support, the first sensor device is connected with a slide, and the slide is moveably connected with the second sensor device, which is (rigidly) attached to the base frame. In a second arrangement the first sensor device is attached to the base frame, the first sensor device is connected with a slide, and the slide is moveably connected with the second sensor device, which is attached to the patient support. In a third arrangement the second sensor device is attached to the patient support, the second sensor device is connected with a slide, and the slide is moveably connected with the first sensor device, which is attached to the base frame. In a fourth arrangement the second sensor device is attached to the base frame, the second sensor device is connected with a slide, and the slide is moveably connected with the first sensor device, which is attached to the patient support. In all four arrangements the first sensor and the second sensor cooperate with each other using a slide, and the slide is provided to receive a force from a sensor device and to apply said force to the other sensor device.

In another preferred embodiment the slide's connection with the corresponding sensor device is supported by a resilient element. The resilient element provides a certain defined tension on the slide and the sensor device respectively. This way, the force measurements in all sensor units can be carried out with a defined sensitivity. Thus, the accuracy and repeatability of the measurements are increased.

According to the invention only a single type of sensor unit is used to be integrated into a hospital bed to measure and characterize both the movements of the patient, and the weight of the patient. Preferably the first sensor is adapted to measure a force component in a vertical direction in order to provide the patient's weight. In a preferred embodiment the first sensor is a reliable and robust strain gauge sensor. Preferably the second sensor is adapted to measure a force component in a horizontal direction in order to provide information about the movements of the patient. In a preferred embodiment the second sensor is a reliable and robust piezo sensor.

Preferably the data device is adapted to provide the patient's weight and to extract special patterns from the measuring data, e.g. heart rate and breathing rate. Furthermore, special movements, e.g. during restless leg syndrome episodes and of course the presence of the patient in the bed can be deduced.

An advantage of the system according to the present invention over state of the art solutions is that it combines three of the most prominent parameters to be monitored (heart rate, breathing rate, weight) in one device. Another advantage of the system is that it allows an unobtrusive monitoring, even in hospital settings. Another advantage of the present system is that it is robust and inexpensive and for system implementation standard components like known force sensors can be used.

These and other aspects of the invention will be described in detail hereinafter, by way of examples, with reference to the following embodiments and the accompanying drawings; in which.

Figure 1:
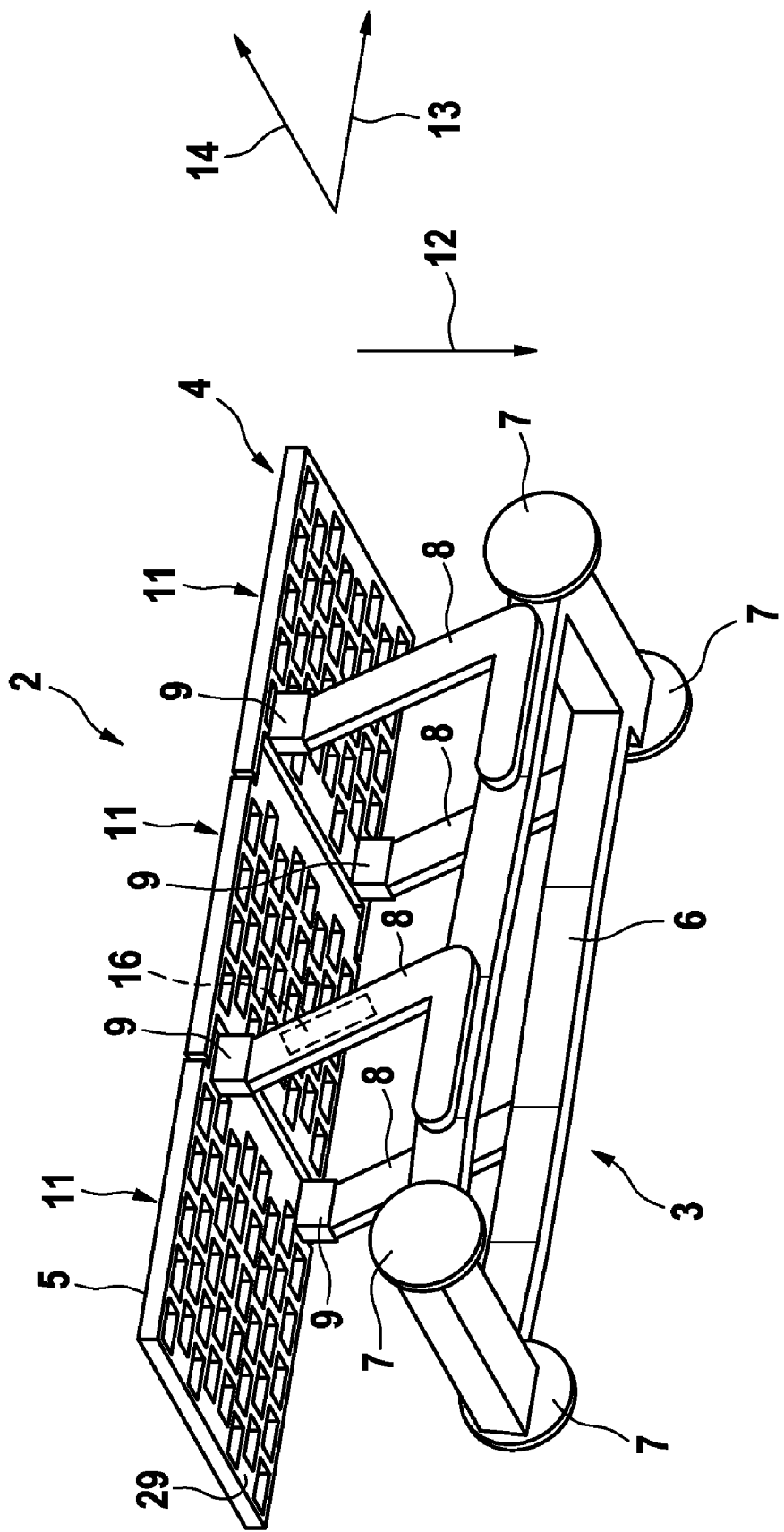
FIG. 1 shows a schematic illustration of hospital bed with four sensor units.

FIG. 1 shows a system 1 according to the invention as applied to a typical mobile hospital bed 2. The bed 2 comprises a base frame 3 and a moveable patient support 4. A patient's mattress (not shown) is positioned on the upside 5 of the patient support 4. The base frame 3 comprises a wheel frame 6 with four wheels 7 and further comprises four bedposts 8 extending upward from the wheel frame 6 to bear the patient support 4. At the upper end of each bedpost 8 identical sensor units 9 are provided. In other words, the sensor units 9 are inherent part of the base frame 3 and the patient support 4 is connected to the upper ends of the four bedposts 8 via said sensor units 9. The bed 2 is configurable by means of hydraulics (not shown) in terms of height of the patient and positioning of different areas 11 of the patient support 4 relative to each other.

The sensor units 9 connect the base frame 3 with the patient support 4 in a movable manner. This means, that, if a patient is located on the mattress, the patient support 4 is moveable downwardly in the direction of arrow 12. If the patient moves, the patient support 4 is moveable sidewards in an arbitrary lateral direction, for example in the direction of arrow 13 or in the direction of arrow 14. Those lateral movements are caused by "large scale" movements, e.g. when the patient turns, or by "small scale" movements, e.g. by the patient's beating heart or by the patient's breathing.

As explained below in a more detailed way each sensor unit 9 comprises two force sensor devices for sensing force components in different directions 12, 13, 14. Each sensor unit 9 comprises a sender 15 for sending measurement data to a data device 16 using a wired or wireless data communication link 17, as explained below. The specific position of the sensor units 9 allows for the measurement of forces of the mattress and patient support 4 on which the patient is lying relative to the base frame 3 of the bed 2. The weight of the patient as well as the patient's movements can be characterized and heart rate and breathing rate of the patient can be extracted. The base frame 3 of the bed 2 can be equipped with other devices, without affecting the measurement.

In the present embodiment the data device 16 is integrated into one of the bedposts 8. The data device 16 comprises an acquisition unit 18 adapted to receive measurement data from the sensor units 9 via the wired or wireless data communication links 17. The data device 16 further comprises a data processing unit 19, which is adapted to perform all tasks of processing and computing of the measured data as well as determining and assessing results. In particular the processing unit 19 is adapted to process the measurement data in order to provide information about the weight, the heart rate and the breath rate of the patient. This is achieved according to the invention by means of a computer software comprising computer instructions adapted for carrying out the steps of the inventive method, when the software is executed in the processing unit 19. The processing unit 19 itself may comprise functional computer modules or units, which are implemented in form of hardware, software or in form of a combination of both. In a preferred embodiment the invention is implemented using a software executed on a dedicated hardware, i.e. the hardware is chosen and/or designed to execute the specific software.

The information about weight, heart rate, breath rate etc. can be stored in the data device 16 and/or displayed to the hospital staff and/or transmitted to an external receiver 20 in order to be stored and/or displayed externally. For this purpose the data device 16 preferably comprises a data storage device (not shown), e.g. a hard disc, and/or a display unit (not shown), e.g. a LED monitor, and/or a transmitter 21, adapted to provide a preferably wireless communication link 22 to the external receiver 20, e.g. using Bluetooth or WLAN standards. The external receiver 20 comprises a LED monitor 23 for displaying the parameter information.

The data device 16 preferably comprises tools to cope with the routines of handling, e.g. a "zero" button to define tare weight, a "hold" button to remember patients weight during manipulations to the patient support 4, e.g. during adding a pillow, etc. Such tools are preferably implemented in form of software modules.

Figure 2:
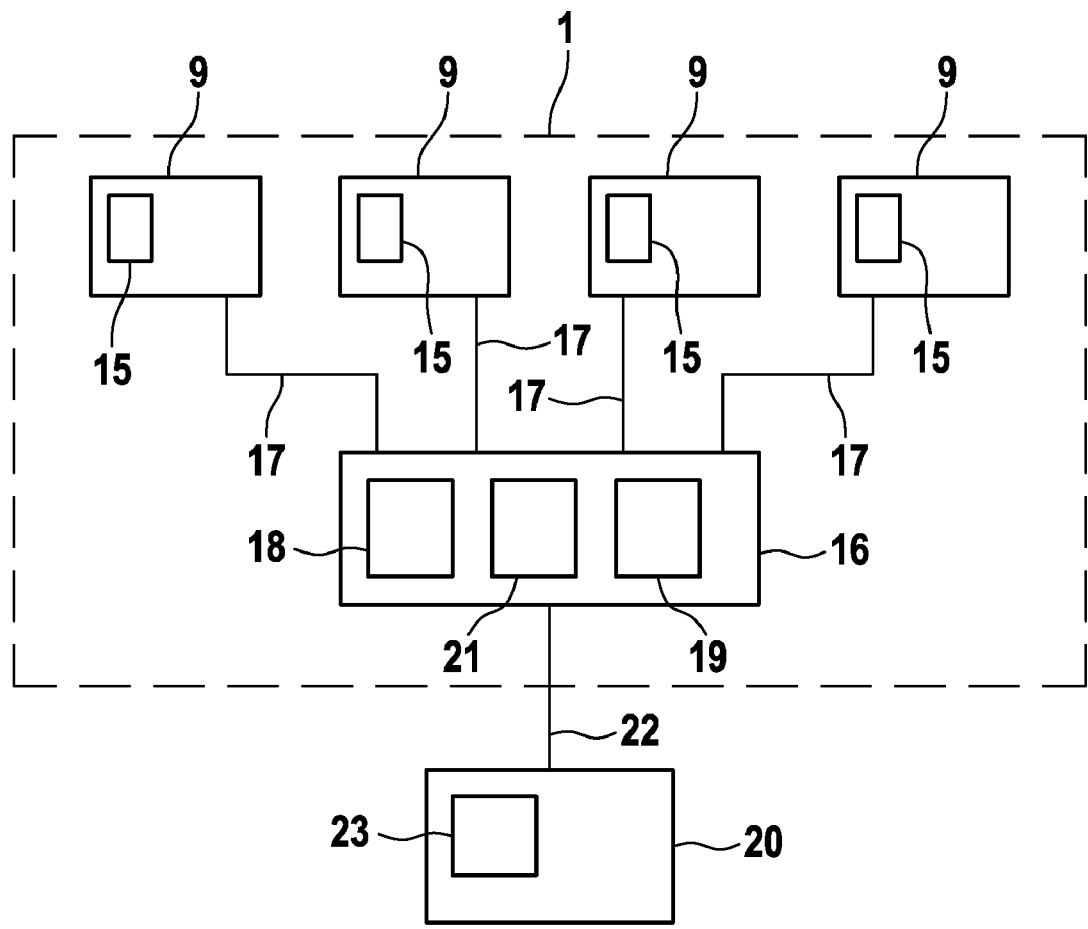
FIG. 2 shows a schematic illustration of a monitoring system.
Figure 3:
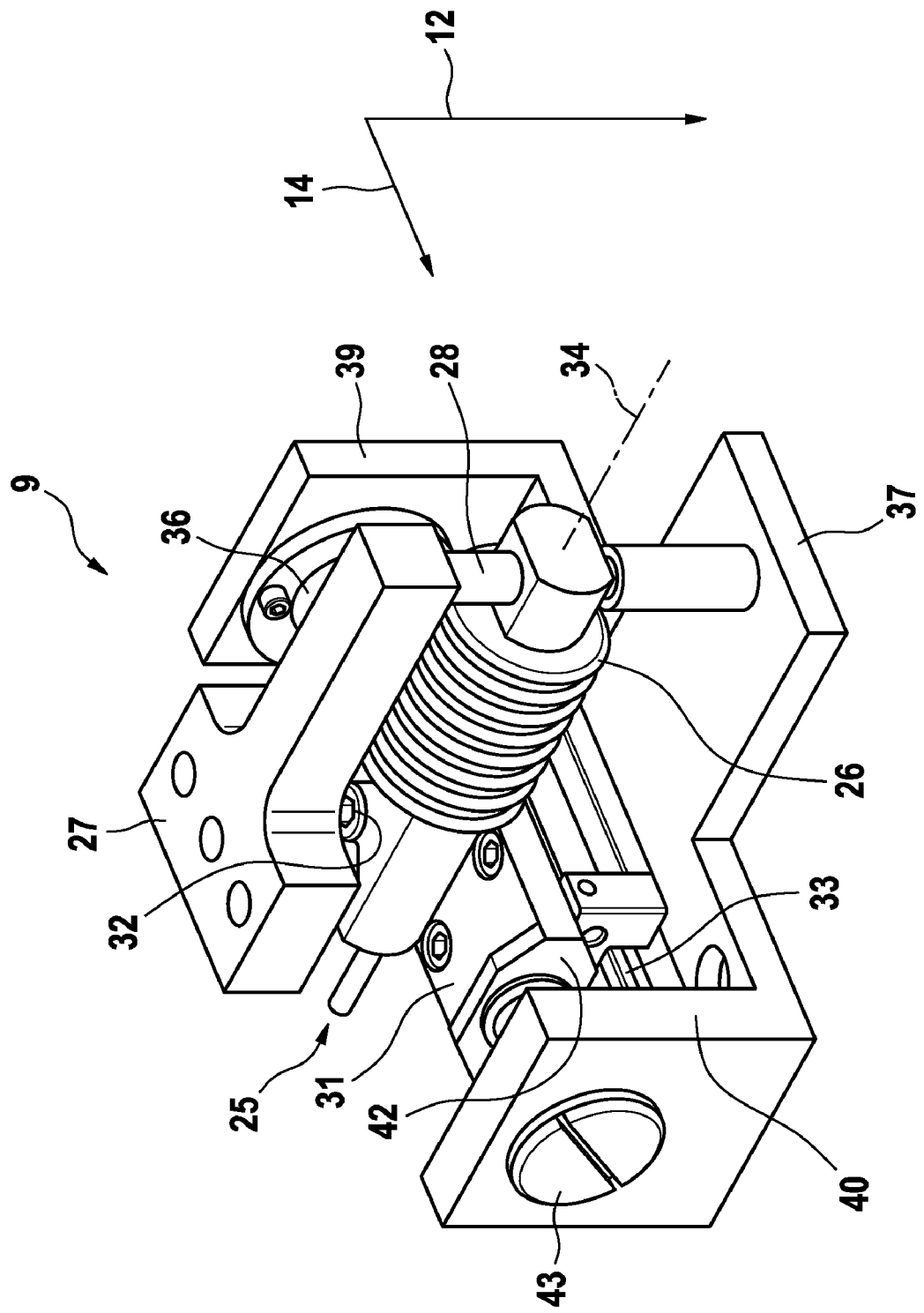
FIG. 3 shows a first illustration of a sensor unit.
Figure 4:
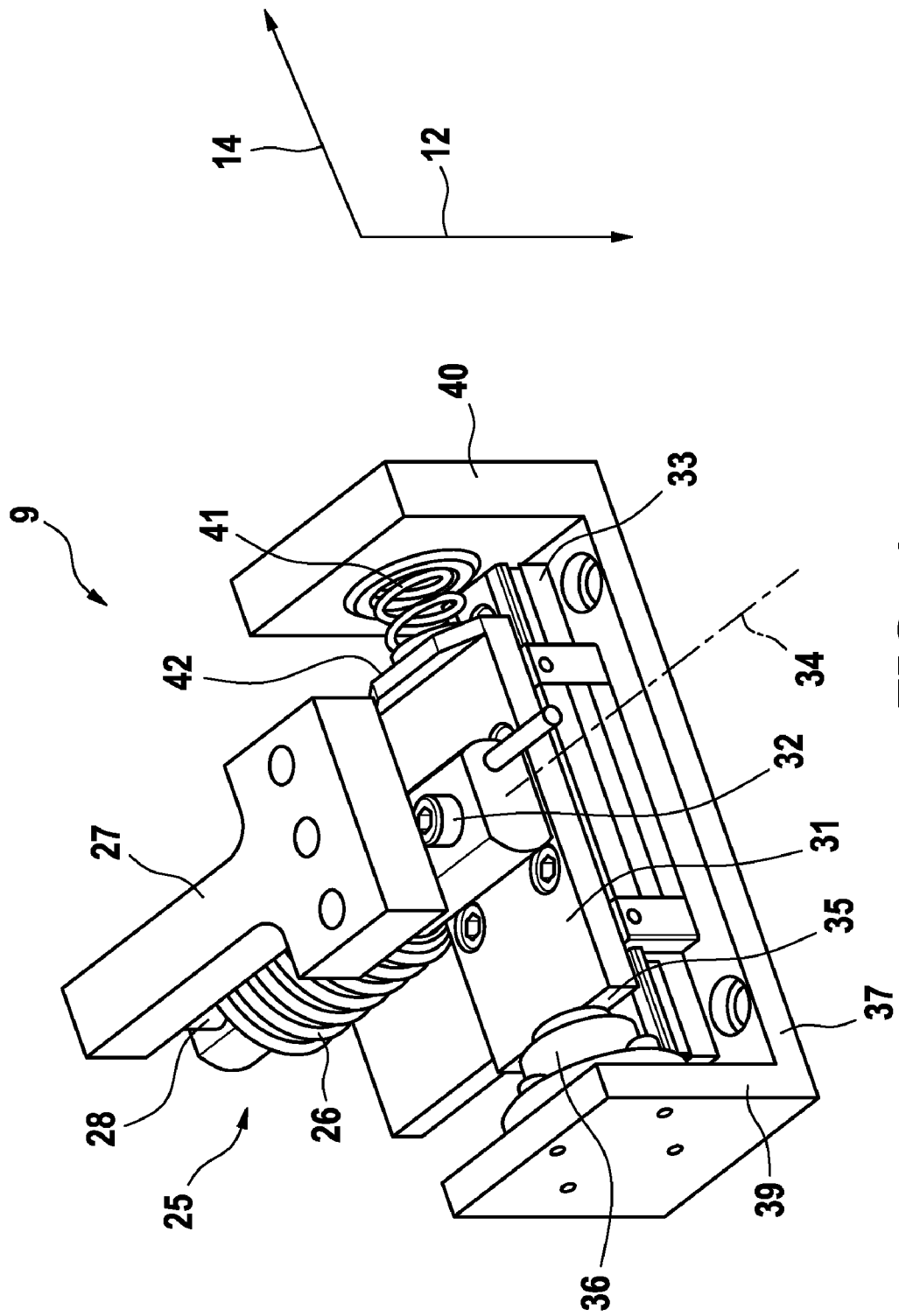
FIG. 4 shows a second illustration of a sensor unit.

In FIGS. 2 and 3 a single sensor unit 9 is shown. In this embodiment a strain gauge sensor 25, acting as first sensor device, is rigidly attached to the patient support 4. The strain gauge sensor 25 is adapted to measure a force component in a vertical direction 12 in order to provide the patient's weight. The strain gauge sensor 25 is mounted horizontally in a protecting box 26 having a cylindrical shape. The one end of the strain gauge sensor 25 is linked with the free end of an upper T-shaped connecting plate 27 by means of a vertical intermediate piece 28. The upper connecting plate 27 is mounted to the bottom side 29 (see FIG. 1) of the patient support 4 by means of three connecting members (not shown). The other end of the strain gauge sensor 25 is linked with a slide 31 by means of a connecting member 32. The slide 31 allows for relative movements of the base frame 3 and the patient support 4. The slide 31 is mounted on a rail element 33. The rail element 33 extends horizontally and perpendicular to the longitudinal axis 34 of the strain gauge sensor 25. One front end 35 of the slide 31 rests against a piezo sensor 36. The piezo sensor 36 acts as second sensor device and is rigidly attached to a mainly U-shaped lower connecting plate 37. The lower connecting plate 37 is connected to the base frame 3 using four connecting members (not shown). The rail element 33 guiding the slide 31 is provided in between the two U-legs 39, 40 of the lower connecting plate 37 and the piezo sensor 36 is mounted on the inside of the first U-leg 39. The piezo sensor 36 is adapted to measure a force component in a horizontal direction, e.g. in direction 13 or 14, in order to provide information about the movements of the patient. In other words, every additional horizontal force component will yield a signal in the piezo sensor 36. The slide 31 is connected with the piezo sensor 36 via a prestressed spiral spring 41. The spiral spring 41, which provides a certain defined tension on the piezo sensor 36, is mounted on the inside of the opposite second U-leg 40, and is connected with the other front end 42 of the slide 31. The initial tension of the spiral spring 41 can be adjusted by means of an adjusting screw 43 on the outside of the second U-leg 40. Instead of a spiral spring 41 other types of resilient elements may be used.

The alignment of the slides 31 in the four sensor units 9 differs for each sensor unit. In a preferred embodiment of the invention the slides 31 are arranged in perpendicular directions, so the movements in both horizontal directions 13, 14 can be detected. For this purpose the sensor units 9 are simply positioned rotated to each other.

In other embodiments of the invention different geometrical arrangements of the sensor units 9 are used, e.g. using tilted angles for performing measurements in any direction (not shown).

In another embodiment the four sensor units 9 used are not all identical. For example only one or two sensor units may comprise a second sensor for measuring the horizontal force component. In another embodiment the sensor units 9 may not all comprise a first sensor for measuring the vertical force component. Preferably a system with three first sensors is used for providing a mechanically stable weight measurement.

In another embodiment a reduced number of sensor units 9 is employed. For obtaining complete parameter information as described above three sensor units 9 are preferably used. However, using only two or even a single sensor unit is possible, depending on the design of the bed and depending on the desired accuracy of the measurement.

In a further embodiment of the invention the sensor type selection as well as the selection of sensor quantity and the positioning of the sensors in the bed 2 is preferably performed depending on the privileged direction of the reclined patient.

In other embodiments of the present invention other types of force or load sensors may be employed.

It will be evident to those skilled in the art that the invention is not limited to the details of the foregoing illustrative embodiments, and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein. It will furthermore be evident that the word "comprising" does not exclude other elements or steps, that the words "a" or "an" do not exclude a plurality, and that a single element, such as a computer system or another unit may fulfil the functions of several means recited in the claims. Any reference signs in the claims shall not be construed as limiting the claim concerned.

REFERENCE NUMERALS

1 System
2 bed
3 base frame
4 patient support
5 upside
6 wheel frame
7 wheel
8 bedpost
9 sensor unit
10 (free)
11 moveable area
12 downward direction
13 lateral direction
14 lateral direction
15 sender
16 data device
17 communication link
18 acquisition unit
19 data processing unit
20 external receiver
21 transmitter
22 communication link
23 LED monitor
24 (free)
25 strain gauge sensor
26 protecting box
27 upper connecting plate
28 intermediate piece
29 bottom side
30 (free)
31 slide
32 connecting member 33 rail element
34 longitudinal axis
35 front end
36 piezo sensor
37 lower connecting plate
38 (free)
39 U-leg
40 U-leg
41 spiral spring
42 front end
43 adjusting screw

The invention claimed is:

1. A system for monitoring a plurality of physiological parameters of a patient in a bed, the system comprising:
 a base frame;
 a patient support;
 a plurality of sensor units mounted between the base frame and the patient support to support the patient support, each of the sensor units including:
  a first sensor device which measures a first force component in a first direction, the first sensor device being attached to one of the patient support and the base frame;
  a rail mounted to the other of the patient support and the base frame;
  a slide which is supported on the rail and movable relative to the rail, wherein the first sensor device is in contact with the slide;
  a second sensor device attached adjacent the rail to interact with the slide to measure a second force component in a second direction, the second direction being different from the first direction; and
 a data device which receives measured force component data from the sensor units and processes the force component data to provide information about the plurality of physiological parameters of the patient.

2. The system as claimed in claim 1, further including: a resilient element which biases the slide against the second sensor device.

3. The system as claimed in claim 1, in which the first sensor device comprises a strain gauge sensor.

4. The system as claimed in claim 1, in which the second direction of the second force component measured by the second sensor device is in a horizontal direction.

5. The system as claimed in claim 1, in which the second sensor device comprises a piezo sensor.

6. The system as claimed in claim 1, wherein the first direction of the component measured by the first sensor device is vertical.

7. The system as claimed in claim 6, wherein the sensor units are arranged such that the second force component measured by at least one of the sensor units is in a first horizontal direction and the second force component force component measured by at least one other of the sensor devices is in a second horizontal direction transverse to the first horizontal direction.

8. A system for monitoring at least respiration and heart rate parameters of a patient in a bed, the system comprising:
 a base frame;
 sensor units mounted to the base frame, each sensor unit including:
  a first sensor device which measures a first force component acting in a first direction on a slide which is movable in a second direction orthogonal to the first direction, the first sensor generating a first signal indicative of the first force component;
  a second sensor device which measures a second force component acting in the second direction on the slide and generates a second signal indicative of the second force component;
 a patient support mounted to and supported by the sensor units and wherein each sensor unit enables relative movement between the base frame and the patient support via the slide; and
 a data device which receives the first and second signals from the sensor units and processes the first and second signals to provide information about the respiration and heart rate parameters of the patient.

9. The system as claimed in claim 8, in which:
 the first force component measured by the first sensor device is in a vertical direction; and
 the second force component measured by the second sensor device is in a horizontal direction.

10. The system as claimed in claim 8, wherein the base frame includes:
 a plurality of bed posts, the sensor units being mounted adjacent an upper end of bed posts.

11. The system as claimed in claim 8, wherein one of the first and second sensor devices is mounted between the patient support and a mechanical member which is supported by the other of the first and second sensor devices, the other of the first and second sensor devices supporting the mechanical member on the base frame.

12. The system as claimed in claim 8, wherein each sensor unit further includes:
 a third sensor device which measures a third force component acting in a third direction transverse to the first and second directions and generates a third signal indicative of the third force, the data device receiving the third signal.

13. The system as claimed in claim 12, wherein each sensor unit further includes:
 a first mechanical member, and a second mechanical member, one of the first, second, and third sensor devices being mounted between the patient support and the first mechanical member, another of the sensor devices being mounted between the first and second mechanical members, and a last of the sensor devices being mounted between the second mechanical member and the base frame.

14. The system as claimed in claim 8, wherein each of the sensor devices includes a strain gauge.

15. A method of monitoring respiration and heart rate parameters of a patient in a bed, the method comprising:
 supporting a plurality of sensor units adjacent an upper end of a base frame;
 supporting a patient support which is adapted to support a mattress on the plurality of sensor units;
 with each sensor unit, measuring:
  at least one first force component acting in a first direction on a slide which is movable relative to one of the base frame and patient support in a second direction and generating first force component data indicative of the measured at least one first force component with a first force sensing device;
  at least one second force component acting on the slide in the second direction and generating second force component data indicative of the measured at least one second force component with a second sensor device, said second direction being different from the first direction;

processing the first force component data and the second force component data to determine the respiration and heart rate parameters of the patient; and displaying the determined respiration and heart rate parameters on a display device.

16. The method as claimed in claim 15, wherein the base frame includes a plurality of bed posts and supporting the sensor units on the base frame includes supporting the sensor units adjacent upper ends of the bed posts.

17. The method as claimed in claim 15, further including:
controlling the base frame to adjust a height of the patient support.

* * * * *